US007587700B2

(12) United States Patent
Nehmadi et al.

(10) Patent No.: US 7,587,700 B2
(45) Date of Patent: Sep. 8, 2009

(54) PROCESS MONITORING SYSTEM AND METHOD FOR PROCESSING A LARGE NUMBER OF SUB-MICRON MEASUREMENT TARGETS

(75) Inventors: Youval Nehmadi, Moddin (IL); Zamir Abraham, Rehovot (IL); Gil Sod-Moriah, Rehovot (IL); Yair Eran, Rehovot (IL); Chen Ofek, Wizman (IL); Yaron Cohen, Givhat-Brener (IL); Ariel Ben-Porath, Gealya (IL)

(73) Assignee: Applied Materials, Israel, Ltd., Rehovot (IL)

( * ) Notice: Subject to any disclaimer, the term of this patent is extended or adjusted under 35 U.S.C. 154(b) by 1064 days.

(21) Appl. No.: 10/817,104

(22) Filed: Apr. 1, 2004

(65) Prior Publication Data

US 2008/0092088 A1  Apr. 17, 2008

Related U.S. Application Data

(60) Provisional application No. 60/491,799, filed on Aug. 1, 2003.

(51) Int. Cl.
*G06F 17/50* (2006.01)
(52) U.S. Cl. ............... 716/19; 716/4; 716/5; 716/6; 716/20; 716/21; 382/144; 324/751; 430/30; 700/121
(58) Field of Classification Search ............... 716/4–6, 716/19–21; 382/144; 324/751; 430/30; 700/121
See application file for complete search history.

(56) References Cited

U.S. PATENT DOCUMENTS 6,392,229 B1 * 5/2002 Dana et al. ............... 250/306

6,559,662 B1    5/2003  Yamada et al.
6,578,188 B1 *  6/2003  Pang et al. .................... 716/19
6,658,640 B2 * 12/2003  Weed ........................... 716/19

(Continued)

FOREIGN PATENT DOCUMENTS

JP         11160402         6/1999

(Continued)

OTHER PUBLICATIONS

Macari et al.; "Automated Contactless SEM Testing for VLSI Development and Failure Analysis"; Reliability Physics Symposium, 1982. 20th Annual; Mar. 1982. pp. 163-166.*

(Continued)

*Primary Examiner*—Naum B Levin
(74) *Attorney, Agent, or Firm*—Tarek N. Fahmi

(57) ABSTRACT

The invention provides a method that includes the stages of: (i) receiving design information representative of a portion of an object that includes sub micron measurement targets, (ii) processing the received design information to provide a large number of measurement targets; and (iii) associating target measurement parameters to each of large number of measurement targets.

The invention provides a system that includes: (i) an interface for receiving design information representative of a portion of a layer of an object that includes sub micron measurement targets; and (ii) a processor, coupled to the interface, for processing the received design information to provide a large number of measurement targets; and for associating target measurement parameters to each of large number of measurement targets.

36 Claims, 8 Drawing Sheets

U.S. PATENT DOCUMENTS

| | | | | |
|---|---|---|---|---|
| 6,868,175 B1 * | 3/2005 | Yamamoto et al. | ........... | 382/145 |
| 6,974,653 B2 * | 12/2005 | Leung et al. | ................... | 430/30 |
| 7,216,311 B2 * | 5/2007 | Tanaka et al. | ................... | 716/4 |
| 7,225,047 B2 * | 5/2007 | Al-Bayati et al. | ............ | 700/121 |
| 7,312,446 B2 * | 12/2007 | Shemesh | ..................... | 250/310 |
| 2001/0019625 A1 * | 9/2001 | Kenan et al. | ................. | 382/144 |
| 2002/0019729 A1 * | 2/2002 | Chang et al. | ................... | 703/6 |
| 2002/0093350 A1 * | 7/2002 | Yamada | ...................... | 324/751 |
| 2005/0146714 A1 * | 7/2005 | Kitamura et al. | ......... | 356/237.2 |

FOREIGN PATENT DOCUMENTS

| | | |
|---|---|---|
| JP | 11257939 | 9/1999 |
| WO | WO-03067653 | 8/2003 |

OTHER PUBLICATIONS

Search Report, "International Searching Authority", PCT/US2004/006634, (Apr. 3, 2004).

* cited by examiner

| site Select Y/N | Site ID | Site Color | IC ID | IC name | Device type | Monitor type | motivation | Conductance Y/N | Material | Location X,Y | Associated image ID |
|---|---|---|---|---|---|---|---|---|---|---|---|
| | | | | | | | | | | | |
| | | | | | | | | | | | |
| | | | | | | | | | | | |
| | | | | | | | | | | | |

Figure 7

PROCESS MONITORING SYSTEM AND METHOD FOR PROCESSING A LARGE NUMBER OF SUB-MICRON MEASUREMENT TARGETS

RELATED APPLICATIONS

The present invention claims priority of U.S. patent application Ser. No. 60/491,799 filed 1 Aug. 2003.

FIELD OF THE INVENTION

The present invention relates to a process monitoring system and method and especially for system and method that allow a large number of measurements.

BACKGROUND

Electronic design automation (EDA) tools are software applications that are applied extensively in the design of integrated circuits and in verification of these designs. EDA tools are used, for example, in logic synthesis, placement and routing of circuit elements, circuit layout and design rule checking. At the end of the design process, a set of reticles (also referred to as masks or templates) is generated for use in producing the integrated circuit (IC). Each reticle corresponds to one layer of the thin film structures that will be fabricated on a semiconductor wafer to produce the IC.

In the fabrication facility (fab), the reticles are used to print the successive circuit layers on the wafer in a photolithographic process. Each wafer undergoes hundreds of processing steps, including not only printing the reticles, but also material deposition, etching, cleaning and polishing. Defects in any of the process steps can substantially reduce the process yield. Therefore, monitoring tools are used to check wafers at nearly every step in the process to verify that the processing tools are functioning properly. Monitoring tools that are used for this purpose include systems for inspection and metrology of integrated circuit structures (typically optical or electron beam-based), as well as systems for electrical testing of circuit components. Reticles are also monitored for defects that may result in defects on the wafer. In the context of the present patent application and in the claims, the term "monitoring" should be understood as including all available modalities for testing wafers and reticles in production for purposes of detecting process or product defects. Monitoring modalities include, but are not limited to, measurement of critical dimensions (CD), film thickness and film composition; defect inspection, review and classification; electrical testing, including in-line and end-of-line tests; profilometry; ellipsometry; reflectometry; particle monitoring; and integrated defect detection and removal, using systems such as the Applied Materials "Bee."

Photolithography is a technique for producing images on semiconductor devices. Typically, an image formed on a mask or "reticle" is transferred to a semiconductor object, or wafer, where it exposes a resist layer placed on the object. It is desired to pattern smaller and smaller features on semiconductor objects, which requires the use of shorter and shorter wavelengths of the light that is used to image the patterns. The minimal printable feature size is referred to as "Critical Dimension".

The measurement of critical dimension includes directing a very narrow electron beam towards a measurement target. This measurement is more time consuming than other measurement or defect detection operation that utilizes a much larger optical beam or a larger electron beam. Typically a limited amount of CD measurement targets are selected manually by experienced engineers that are familiar with the manufacturing process.

There is an ever growing need to increase and even dramatically increase the amount of CD measurements that can be done in a reasonable time frame. This need may steam from applying OPC techniques that are aimed to improve the resolution of pattern printing.

The purpose of OPC is to compensate for optical distortions which typically arise when different features on the stencil mask are close to each other, by introducing corrections on the mask itself. These "corrections" are intentional distortions to the design as it appears on the mask that are designed to counteract the optical proximity distortions created during photo-lithography.

The complexity of OPC as well as the reducing wavelengths of lithography radiation does not allow to accurately simulate or otherwise predict the actual pattern that will be printed during a lithography process, given a certain reticle.

In order to overcome this difficulty test reticles are manufactured. These test reticles include a large number of structures that are printed on a test wafer that is then examined to assist in determining how to shape a reticle in order to achieve a desired pattern, and which "corrections" shall be added according to the OPC techniques.

Various types of OPC algorithms are applied to different features, with the purpose of testing empirically, by executing at least several of the manufacturing steps for patterning the wafer, which OPC feature resulted in the best pattern on the wafer. Such experiments require that measurements, such as those performed by CD measurement tools, be performed over thousands of sites per wafer, rather than the typical 5-20 CD measurement sites used for monitoring a production of a wafer. The results of those measurements must be compared to the target values as set forth by the designers of the IC.

SUMMARY OF THE INVENTION

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

The invention provides a method that includes the stages of: (i) receiving design information representative of a portion of a layer of an object; (ii) processing the received design information to provide a large number of measurement targets; and (iii) associating target measurement parameters to each of large number of measurement targets. The object includes multiple sub micron measurement targets and can be, for example, an integrated circuit, a reticle and the like.

The invention provides a system that includes: (i) an interface for receiving design information representative of a portion of a layer of the object; and (ii) a processor, coupled to the interface, for processing the received design information to provide a large number of measurement targets; and for associating target measurement parameters to each of large number of measurement targets.

BRIEF DESCRIPTION OF THE DRAWINGS

Reference is made to the attached drawings, wherein elements having the same reference numeral designations represent like elements throughout, and wherein:

FIGS. 7-8 illustrate means for automatically inserting measurement target selection criteria, according to embodiments of the invention.

DESCRIPTION OF THE INVENTION

The term "object that includes sub micron measurement targets" refers to an object that has multiple sub-micron features, structural elements and the like. The features an/or structural elements are subjected to measurements by a measurement tool. A non limiting example of such an object is a integrated circuit, die, dice, wafer, reticle, MEMS, flat display panels, and the like. It is noted that the invention can be applied to monitor the manufacturing process of multiple layered objects as well as single layered objects.

For convenience of explanation it is assumed that the object is a multi-layered integrated circuit.

Figure 1:
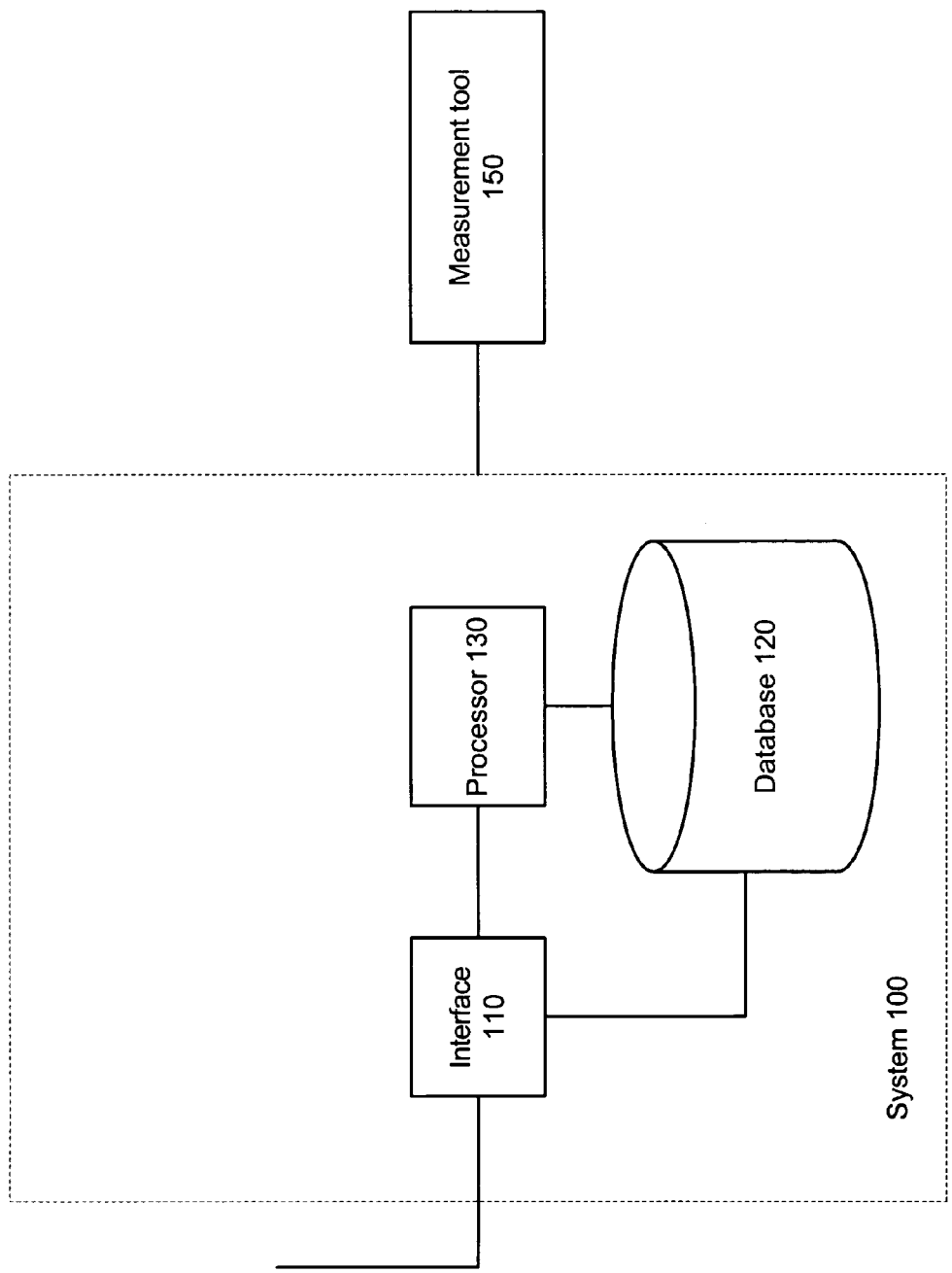
FIG. 1 illustrates a system, as well as a measurement tool, according to an embodiment of the invention.

FIG. 1 illustrates system 100 as well as a measurement tool 150 such as CD-SEM 3D of Applied Materials Inc. of Santa Clara Calif. The system includes an interface 110 that receives an EDA file that describes at least a part of one layer of and sends it to a database 120. Processor 130 accesses the stored information and process it to provide a large number of measurement targets. The processor 130 also associates target measurement parameters to each of large number of measurement targets. This processing stage is further illustrated in the following figures. It is noted that a designed layer is processed to provide the image that will be actually printed on the IC. This processing stage or even a part of this stage can be implemented by system 100.

The target measurement parameters of said large number of sites are sent to measurement tool 150 that performs in response multiple measurements to provide measurement results. The results can be sent back to system 100 that may store them and even process them.

Figure 8:
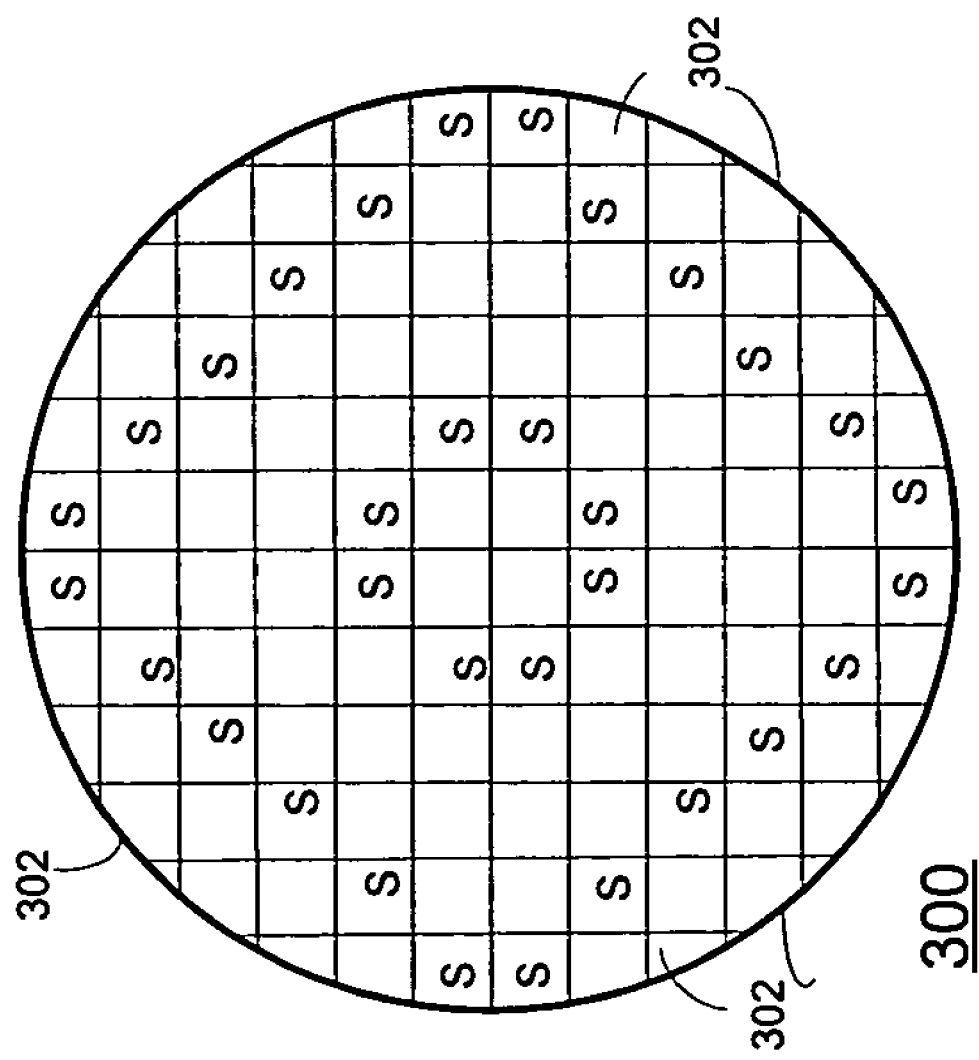

The selection of measurement targets can be responsive to various parameters that are provided by a user. FIG. 7 illustrates an exemplary table 200 that allows a user to select targets or select target parameters that assist in automatic selection of the targets. The table 200 allows to insert and/or display various target parameters, IC parameters and additional information such as site select Y/N box 202 (indicates if a target was automatically selected, allows to manually select a target), site ID 204 (each measurement site is associated with a unique identification number), site color 206 (indicating how to render the site in a visual representation such as a wafer map), IC ID 208 (each IC is associated with a unique ID), IC name 210 (each IC is often associated with a name that further assists in its identification), device type 212 (describes the target—a transistor, a conductor . . . ), Monitor type 214 (describes what is the type of measurement that is required—line width, hole diameter, . . . ), motivation 216 (describes the purpose of the measurement), conductance Y/N box 218, material 220, location X,Y 222, and associated image ID 224 (this information allows to retrieve an image of a vicinity of the target). An additional means for selecting sites, on a die basis, is illustrated in FIG. 8. An image of a wafer 300 having multiple dice 302 is shown. Some dice include measurement sites (denoted "S"). This display can be used to select dice or/and to display previously selected dice.

Figure 2:
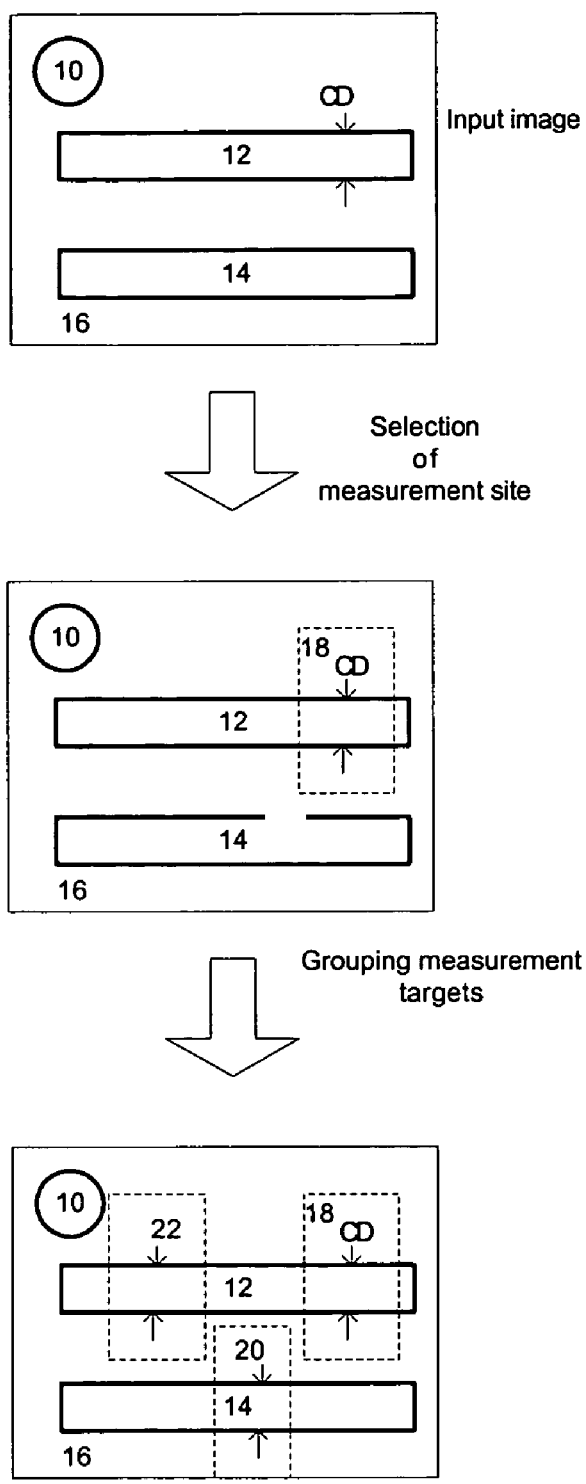
FIG. 2 illustrates an image of a measurement site during various processing stages, according to an embodiment of the invention.

FIG. 2 illustrates an image 16 of a measurement site during various processing stages, according to an embodiment of the invention. The image 16 includes two horizontal lines 12 and 14 and a unique feature 10. The measurement target is selected to be line 12 that is adjacent to unique feature 10 and the required measurement is a CD measurement. The CD measurement will be done within a measurement window 18.

FIG. 2 also illustrates a grouping of three CD measurements within windows 18, 20 and 22. The grouping of measurements reduces the amount of mechanical movements and target site location processes. Thus, process stages that are associated with measurement targets that are positioned at the same filed of view can be performed once, while stages that are unique for each measurement target are repeated for each measurement target.

Figure 3:
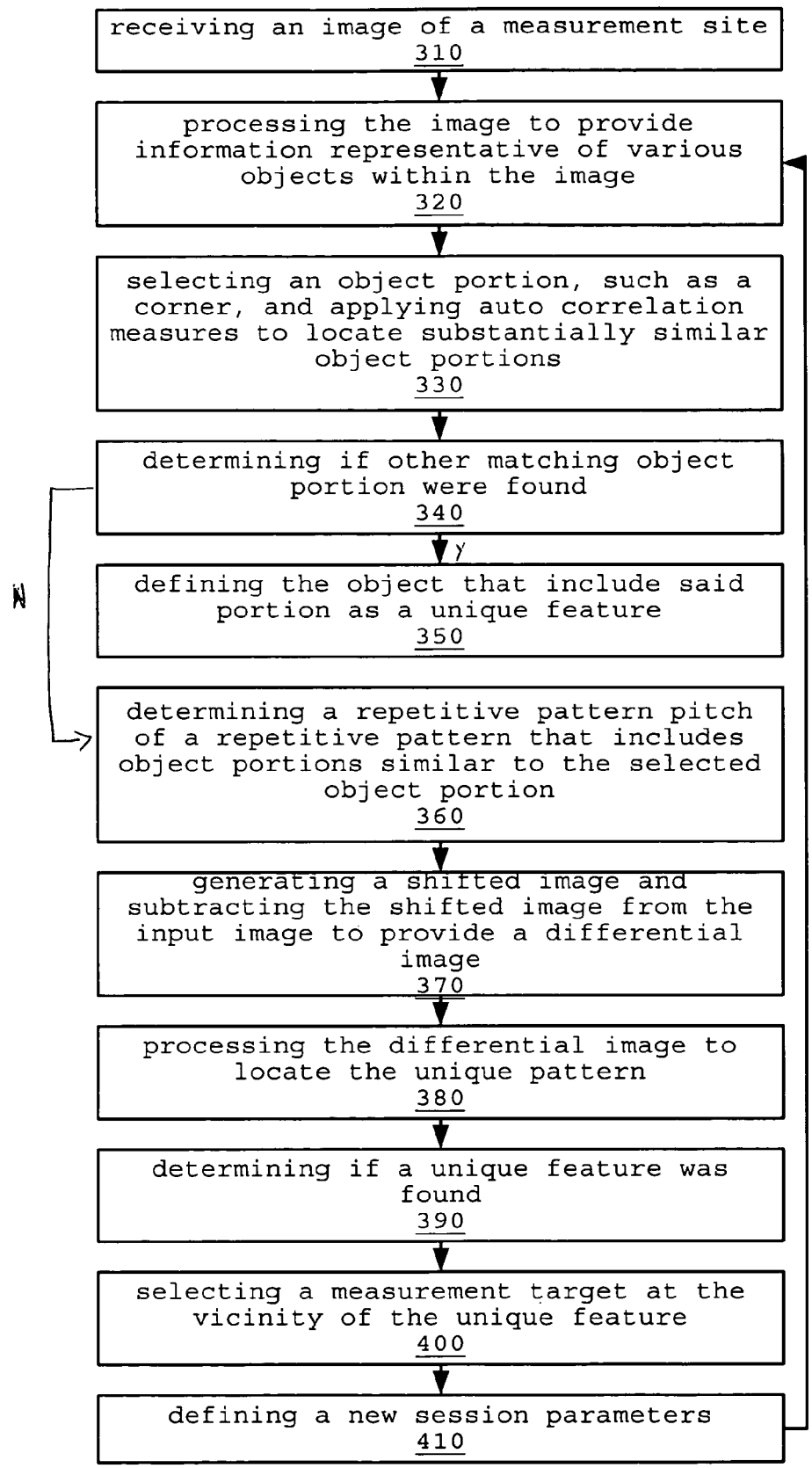
FIG. 3 illustrates a process for locating a measurement target, according to an embodiment of the invention.

FIG. 3 illustrates a process 300 for locating a measurement target, according to an embodiment of the invention. Process 300 starts by stage 310 of receiving an image of a measurement site.

Stage 310 is followed by stage 320 of processing the image to provide information representative of various objects within the image. This stage may include providing information representative of the location of lines, the line orientations, the presence of corners and the like.

Figure 4:
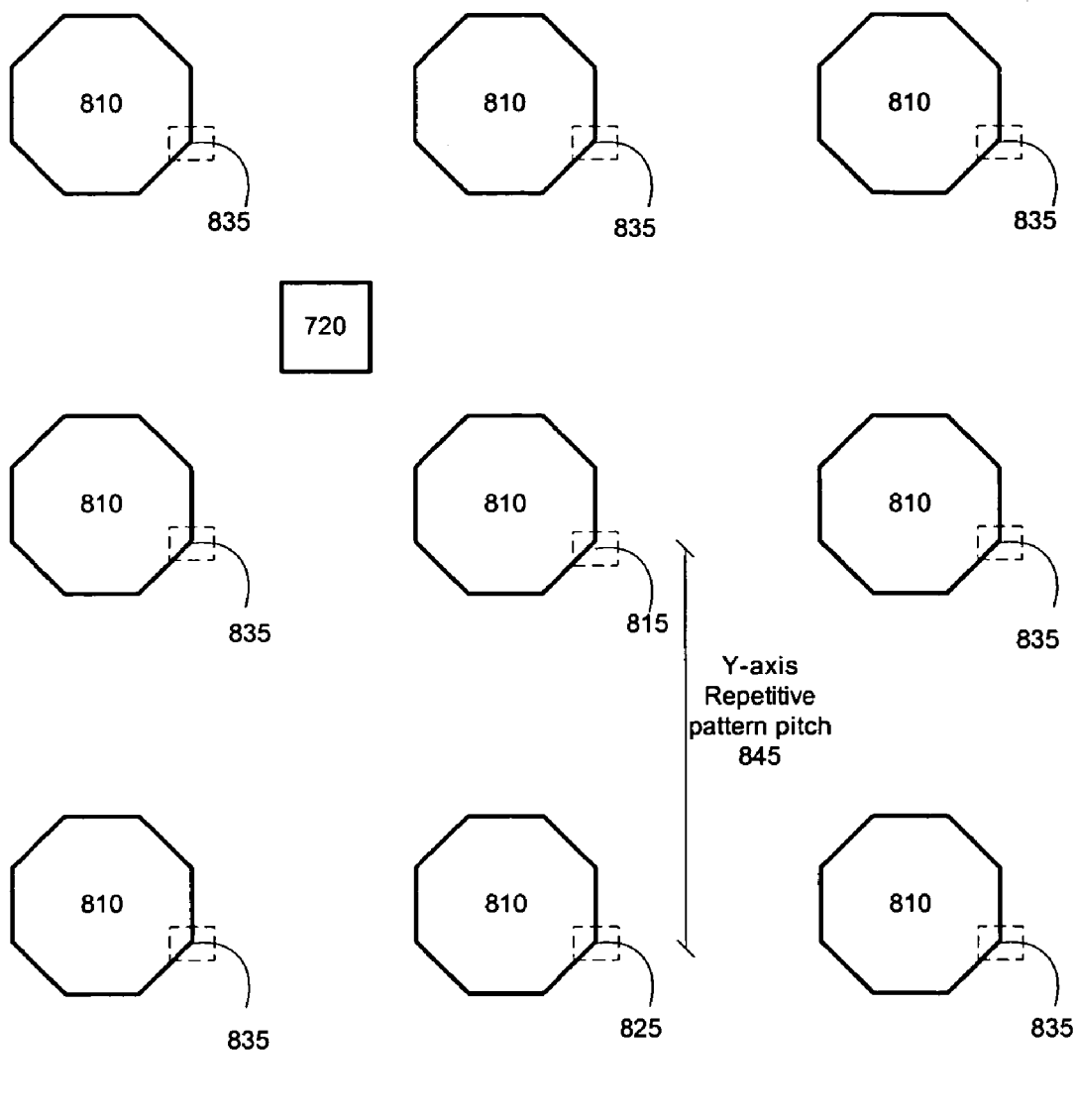
FIGS. 4-5 illustrate various images obtained during the process of FIG. 3, according to an embodiment of the invention.

Stage 320 is followed by stage 330 of selecting an object portion, such as a corner, and applying auto correlation measures to locate substantially similar object portions. Conveniently, the selected object portion is a corner defined by two lines. The angle between said lines can be about ninety degrees, but this is not necessarily so. That corner shall be distant from the image boundaries. If the image has already been processed during an iteration of any of steps 330-370 it is better to select a corner that was not previously selected and does not belong to an object that was previously selected. Preferably, the corner shall be positioned at a certain distance that is responsive to the field of view of the measurement tool. Referring to FIG. 4, illustrating an image of an array 800 of objects 810 that also includes a unique rectangular feature 720. Stage 330 includes selecting a lower right corner 815 of a certain object 810.

Stage 330 is followed by stage 340 of determining if other matching object portions were found. If the answer is positive stage 340 is followed by stage 350 of defining the object that includes said portion as a unique feature. If the answer is positive then stage 340 is followed by stage 360 of determining a repetitive pattern pitch of a repetitive pattern that includes object portions similar to the selected object portion. This determination may involve a single directional processing of the image or a two dimensional processing of the image. Referring to FIG. 4 that illustrates the selected corner 815 as well as other similar corners 825 and 835 that define a repetitive pattern. It is assumed that the pitch is defined by the vertical distance between the selected corner 815 and an adjacent corner 825 located below the selected corner.

Figure 5:
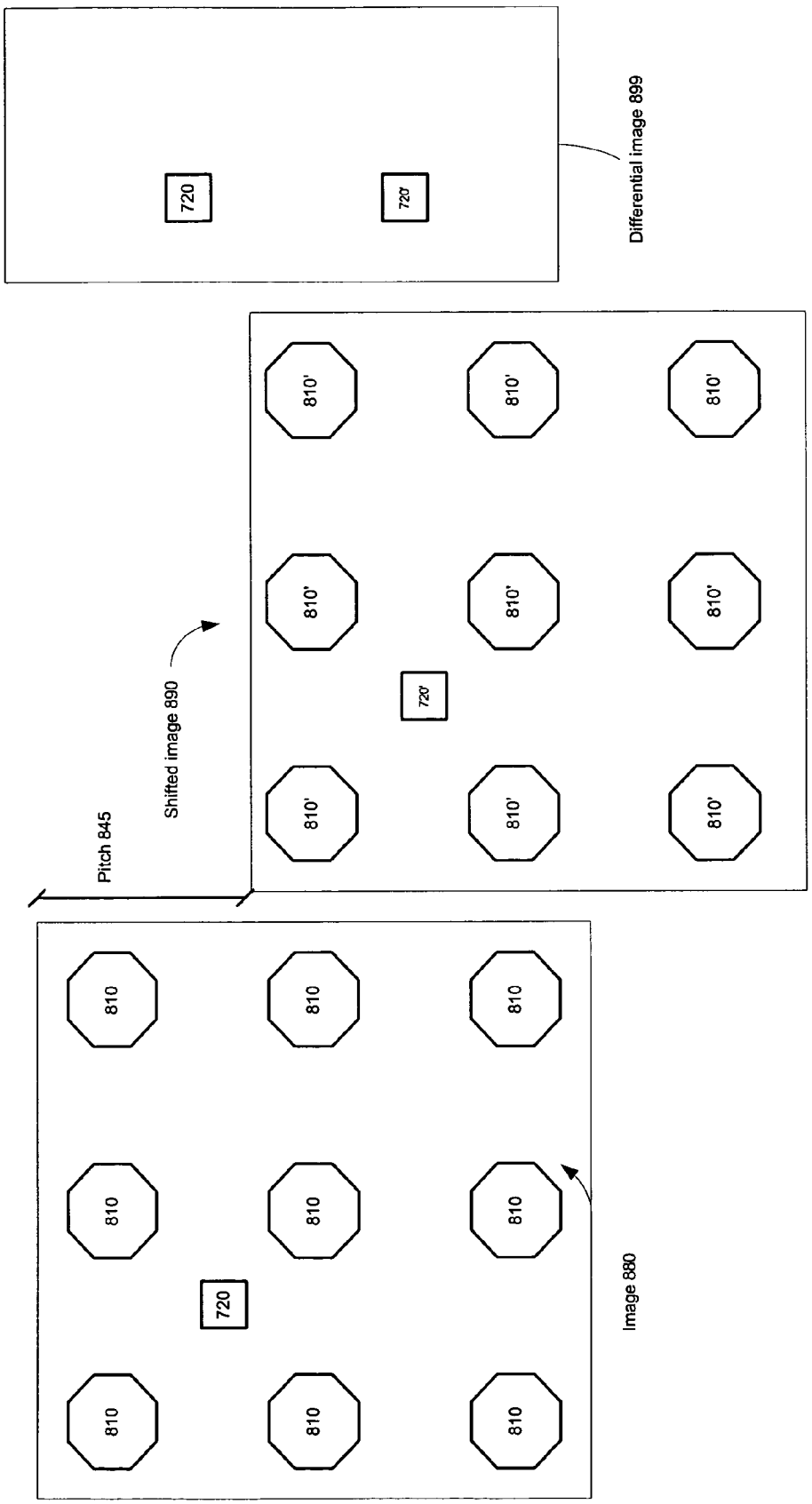

Stage 360 is followed by stage 370 of generating a shifted image and subtracting the shifted image from the input image to provide a differential image. The shifted image is shifted by a repetitive pattern pitch in response to the input image. FIG. 5 illustrates the subtraction of the differential image 890 from an input image 880 to provide a differential image 899. The subtraction will remove all objects 810 from the differential image. Only the unique rectangular feature 720 and a shifted unique rectangular feature 720' remain in the differential image 899.

Stage 370 is followed by stage 380 of processing the differential image to locate the unique pattern. Stage 380 is followed by query stage 390 of determining if a unique feature was found. If the answer is positive stage 390 is followed by stage 400 of selecting a measurement target at the vicinity of the unique feature. Else, stage 390 is followed by stage 410 of defining new session parameters and jumping to stage 320 and even defining new object patterns, finding new repetitive pattern pitches and the like.

Auto focus targets can be located by processing the input image or the information generated during stage 320. According to another embodiment of the invention an auto focus target is located by: (i) dividing the image to multiple sub-images. (ii) calculating the accumulative length of lines located within each sub-image, and (iii) selecting the sub-window that includes the highest aggregate line length as an auto focus target.

According to an embodiment of the invention once a unique feature is found that unique feature as well as an adjacent feature are defined as the unique feature. Referring to FIG. 5 the unique rectangular feature 720 as well as an adjacent object 810.

Figure 6:
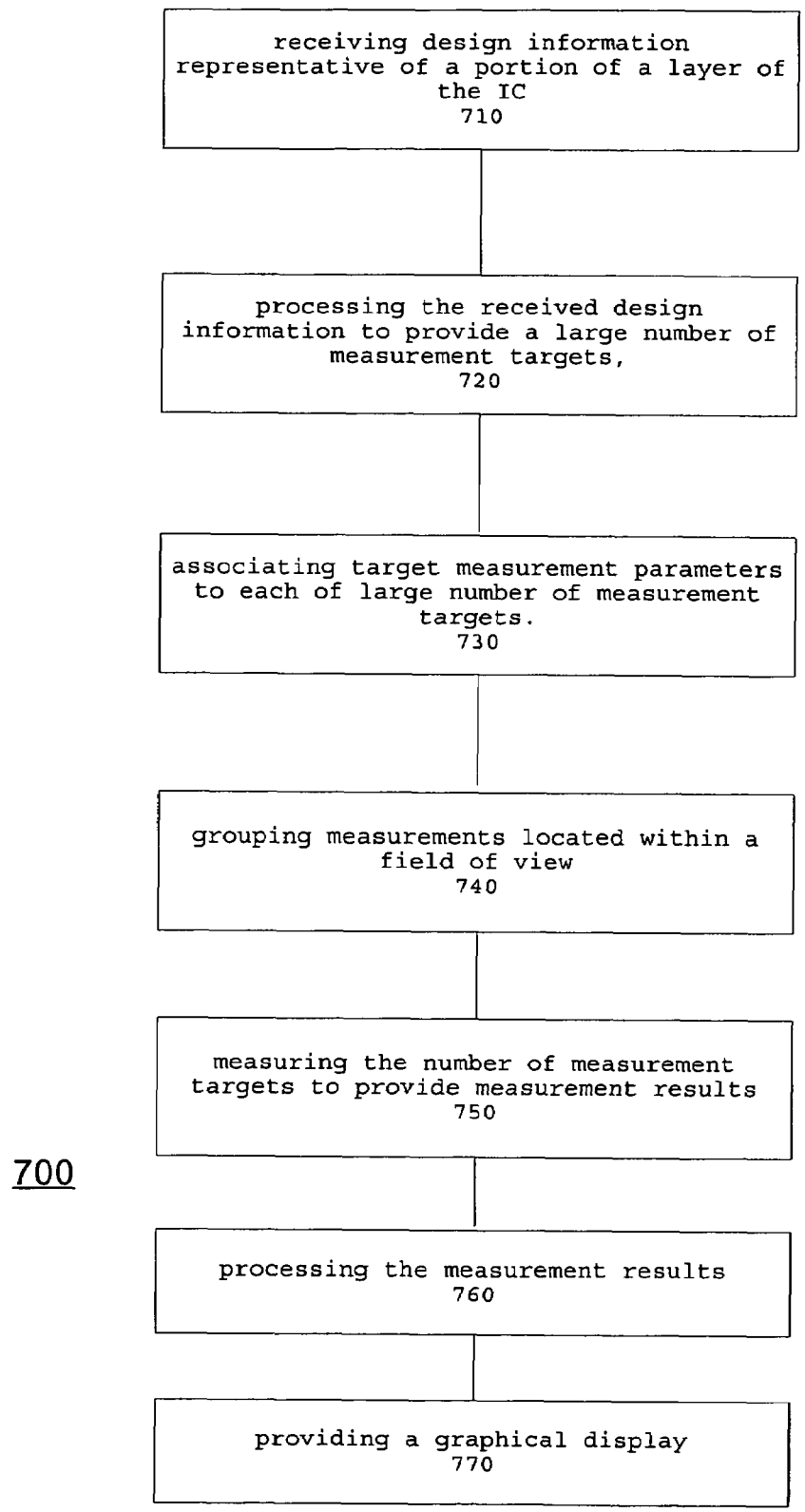
FIG. 6 is a flow chart illustrating a method, according to an embodiment of the invention.

FIG. 6 illustrates a method 700 that includes stage 710 of receiving design information representative of a portion of a layer of the IC, stage 720 of processing the received design information to provide a large number of measurement targets, and stage 730 of associating target measurement parameters to each of a large number of measurement targets.

According to various embodiments of the invention the measurement parameters include location information representative of a location of the measurement site. The location information may include an image of a measurement site that comprises the measurement target. The measurement parameters may include a measurement field of view and/or an electron beam parameter.

Stage 730 may include determining a presence of a unique feature within a measurement site that comprises a measurement target. The determination may involve at least a portion of an image of the measurement site. Said processing may involve applying auto-correlation operation. The process may include locating a repetitive pattern.

Conveniently, stage 720 includes locating auto focus targets. Preferably, each measurement target or each group of measurement targets are associated with an auto focus target.

According to an embodiment of the invention the method further includes a stage 740 of grouping measurements located within a field of view of a measurement tool. Said grouping process is further illustrated at FIG. 2.

Conveniently, stage 720 includes selecting measurement targets associated with optical proximity correction. The selection may include selecting measurement targets in view of a potential measurement target list or table.

Optionally, stage 740 (or stage 730) is followed by stage 750 of measuring the large number of measurement targets, in response to the target measurement parameters, to provide measurement results. Stage 750 may include CD measurement but this not necessarily so. Conveniently the measurement includes locating measurement sites, locating measurement targets within the measurement site, scanning the measurement targets with an electron beam and the like.

Conveniently, stage 750 is followed by stage 760 of processing the measurement results to provide an indication about the fabrication process. This processing stage may include comparing the currently obtained results to previously obtained measurement results. Alternatively or additionally, stage 760 includes comparing the measurement results to expected measurement results. Stage 760 may include determining optimal design features. Alternatively or additionally said stage may include processing the measurement results and design requirements of the IC.

Stage 760 is followed by optional stage 770 of providing a graphical display representative of the measurement results.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein. Further, the description is intended to be descriptive and not limiting.

What is claimed is:

1. A method, comprising:
   receiving, via an interface, design information representative of a portion of a layer of an object that comprises sub-micron measurement targets from a data store;
   storing the received design information in a database;
   accessing, with a processor, the stored design information;
   processing, with the processor, the stored design information to provide a large number of measurement targets, wherein a measurement target is a sub-micron area located on the layer of the object and the processing includes determining information that is representative of an object included in the portion of the layer of the object that comprises sub-micron measurement targets;
   associating, with the processor, target measurement parameters to each of the large number of measurement targets, wherein the target measurement parameters comprise at least one of location information representative of a location of a target measurement on the layer of the object, a measurement field of view, and an electron beam parameter, wherein associating target measurement parameters comprises determining a presence of a unique feature within a measurement site that comprises a measurement target by processing, using an auto-correlation operation, at least a portion of an image of the measurement site;
   measuring, by a measurement tool, each measurement target of the large number of measurement targets using a target measurement parameter associated with each of the measurement targets; and
   processing, by the processor, the measurement results.

2. The method of claim 1 wherein the location information comprises an image of a measurement site that comprises the measurement target.

3. The method of claim 1 wherein the said processing comprises locating a repetitive pattern.

4. The method of claim 1 further comprising grouping measurements located within a field of view of a measurement tool.

5. The method of claim 1 wherein the stage of processing comprising selecting measurement targets associated with optical proximity correction.

6. The method of claim 1 further comprising measuring the large number of measurement targets, in response to the target measurement parameters, to provide measurement results.

7. The method of claim 6 wherein the stage of measuring comprises scanning measurement targets with an electron beam.

8. The method of claim 6 wherein the measurements comprise CD measurements.

9. The method of claim 6 further comprising processing the measurement results to provide an indication about the fabrication process.

10. The method of claim 9 wherein the measurement results are compared to previously obtained measurement results.

11. The method of claim 9 wherein the measurement results are compared to expected measurement results.

12. The method of claim 9 wherein the processing is followed by providing a graphical display representative of the measurement results.

13. The method of claim 9 wherein the processing comprises determining optimal design features.

14. The method of claim 9 wherein the processing comprises processing the measurement results and design requirements of the IC.

15. The method of claim 1 wherein the stage of measurement comprising a stage of locating a vicinity of a measurement target and a stage of detecting the measurement target by using image processing measures.

16. The method of claim 1 wherein the stage of providing a large number of measurement targets further comprises locating auto focus targets.

17. The method of claim 1 wherein each measurement target is associated with an auto focus target.

18. A system, comprising:
a data store for providing design information representative of a portion of a layer of an object that comprises sub micron measurement targets;
an interface, coupled to the data store, for receiving the design information representative of a portion of a layer of an object that comprises sub micron measurement targets; and
a database, coupled to the interface and a processor, for storing the received design information;
the processor, coupled to the interface and database, for accessing the stored design information, processing the stored design information to provide a large number of measurement targets, wherein the processing includes determining information that is representative of an object included in the portion of the layer of the object that comprises sub-micron measurement targets and each measurement target is a sub-micron area located on the layer of the object, and for associating target measurement parameters to each of the large number of measurement targets, wherein the target measurement parameters comprise at least one of location information representative of a location of a target measurement, a measurement field of view, and an electron beam parameter; and
a measurement tool, coupled to the processor, for measuring each measurement target of the large number of measurement targets using a target measurement parameter associated with each of the measurement targets, wherein the processor is adapted to process measurement results of the measurement tool to determine a presence of a unique feature within a measurement site that comprises a measurement target by processing, using an auto-correlation operation, at least a portion of an image of the measurement site.

19. The system of claim 18 wherein the location information comprises an image of a measurement site that comprises the measurement target.

20. The system of claim 18 wherein the processor is adapted to locate a repetitive pattern during the processing of the portion of the image.

21. The system of claim 18 wherein the processor is further adapted to group measurements located within a field of view of a measurement tool.

22. The system of claim 18 wherein the processor is adapted to select measurement targets associated with optical proximity correction.

23. The system of claim 18 further comprising a measurement tool adapted to measure the large number of measurement targets, in response to the target measurement parameters, and to provide measurement results.

24. The system of claim 23 wherein the measurement tool is adapted to scan the measurement targets with an electron beam.

25. The system of claim 23 wherein the measurements tool is adapted to perform CD measurements.

26. The system of claim 23 wherein the measurement tool is adapted to locate a vicinity of a measurement target and then to detect the measurement target by using image processing measures.

27. The system of claim 23 wherein the measurement tool is adapted to locate auto focus targets.

28. The system of claim 27 wherein each measurement target is associated with an auto focus target.

29. The system of claim 18 further adapted to send the target measurement results to a measurement tool.

30. The system of claim 29 further adapted to receive measurement results from the measurement tool.

31. The system of claim 30 further adapted to process the measurement results to provide an indication about the fabrication process.

32. The system of claim 31 further adapted to provide a graphical display representative of the measurement results.

33. The system of claim 30 further adapted to compare the measurement results with previously obtained measurement results.

34. The system of claim 30 further adapted to compare the measurement results with expected measurement results.

35. The system of claim 30 wherein the processor is adapted to determine optimal design features in response to the measurement results.

36. The system of claim 30 wherein the processor is adapted to determine optimal design features in response to design requirements of the IC.

* * * * *